United States Patent [19]

Jiang et al.

[11] Patent Number: 5,480,963
[45] Date of Patent: Jan. 2, 1996

[54] ABSORBABLE COPOLYMERS DERIVED FROM TRICARBOXYLIC ACIDS AND SURGICAL ARTICLES MADE THEREFROM

[75] Inventors: Ying Jiang, North Haven; John S. Bobo, Guilford; Elliott A. Gruskin, Killingworth, all of Conn.

[73] Assignee: United States Surgical Corporation, Norwalk, Conn.

[21] Appl. No.: 279,126

[22] Filed: Jul. 22, 1994

[51] Int. Cl.$^6$ .................................................. C08G 63/12
[52] U.S. Cl. .................. 528/350; 424/78.37; 514/772.3; 514/772.6; 528/271; 528/272; 606/228
[58] Field of Search ...................... 424/78.37; 514/772.3, 514/772.6, 271; 528/272, 350; 606/228

[56] References Cited

U.S. PATENT DOCUMENTS

| 3,661,955 | 5/1972 | Centolella et al. | |
|---|---|---|---|
| 4,481,353 | 11/1984 | Nyilas et al. | 528/303 |
| 4,594,407 | 6/1986 | Nyilas et al. | 528/272 |
| 5,026,821 | 6/1991 | Boustta et al. | 528/350 |
| 5,092,883 | 3/1992 | Eppley et al. | 623/11 |
| 5,187,150 | 2/1993 | Speiser et al. | 514/2 |

FOREIGN PATENT DOCUMENTS

WO88/01155  2/1988  WIPO.

OTHER PUBLICATIONS

"Synthesis and Biodegration of Copolyesters from Citric Acid and Glycorol", *Polymer Bulletin*, vol. 19, pp. 365–370 (1980).

*Primary Examiner*—James J. Seidleck
*Assistant Examiner*—Shelley A. Dodson

[57] ABSTRACT

Bioabsorbable copolymers are derived from tricarboxylic acids and triols. The copolymers are useful in forming surgical articles including, sutures, suture coatings, and gels for promoting tissue repair.

16 Claims, 1 Drawing Sheet

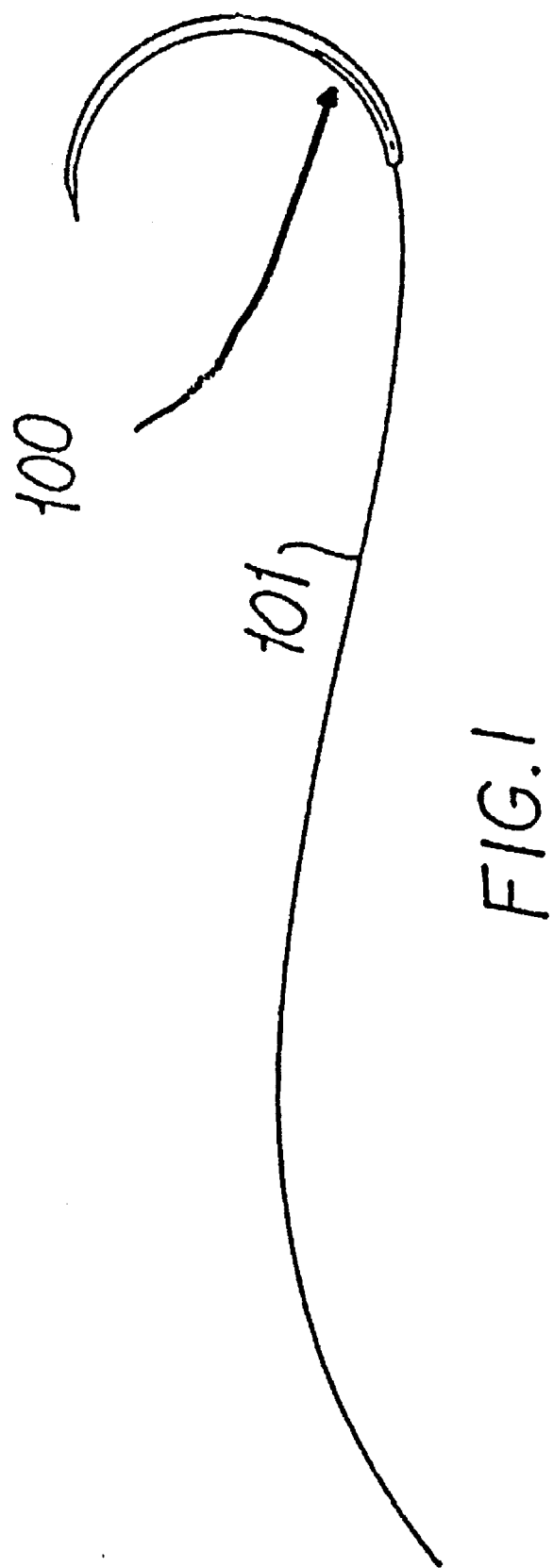

ABSORBABLE COPOLYMERS DERIVED FROM TRICARBOXYLIC ACIDS AND SURGICAL ARTICLES MADE THEREFROM

BACKGROUND OF THE INVENTION

1. Technical Field

Bioabsorbable copolymers having units derived from tricarboxylic acids and triols are described herein. Surgical articles are made from such copolymers including articles for promoting the growth of soft tissue.

2. Background of the Related Art

Polymers having units derived from citric acid have been described for various purposes. For example, U.S. Pat. No. 3,661,955 discloses polyesters of citric acid and sorbitol useful as intermediates in the manufacture of medicine, emulsifiers and as additives to yeast raised products. As another example, U.S. Pat. No. 5,026,821 discloses hydrophilic polymers composed of polyamides resulting from the condensation of citric acid with diamines. The polymers are employed as carriers or reservoirs for the controlled release of drugs, as sutures, surgical prostheses, and surgical adhesives. However, these patents do not describe copolymers including monomeric units derived from tricarboxylic acid and monomeric units derived from a triol, wherein the copolymer includes a substituent which provides a net surface charge.

It has been postulated that the presence of a net surface charge on certain substances can promote wound healing. For example, U.S. Pat. Nos. 4,988,358 and 5,092,883 disclose beads having chemically induced surface charges for promoting tissue growth which are produced by attaching functional groups to a dextran matrix. As another example, Patent No. WO 88/01155 discloses biomaterial implants derived from glutaraldehyde-treated animal tissue covalently bonded to a compound which imparts a net charge to the implant to prevent detrimental calcification of the implant. These publications likewise do not describe copolymers which include a proportion of monomeric units derived from a tricarboxylic acid and a proportion of monomeric units derived from a triol. Nor is the addition of a charge inducing substituent to such copolymers described.

SUMMARY OF THE INVENTION

Novel bioabsorbable copolymers are obtained by polymerizing tricarboxylic acids and triols. Preferred tricarboxylic acids are Kreb's cycle tricarboxylic acids. Such as, for example, citric acid. The present copolymers which include a proportion of monomeric units derived from tricarboxylic acids and a proportion of monomeric units derived from triols can also have a net surface charge for promoting soft tissue growth. The charge carrying copolymers can be cross-linked and are useful for forming surgical articles, such as, for example, cross-linked gels or suture coatings. In a particularly useful embodiment, the copolymer can be used to fabricate a gel or other surgical article for promoting soft tissue growth.

BRIEF DESCRIPTION OF THE DRAWINGS

FIG. 1 is a depiction of a needled suture in accordance with the present invention.

DETAILED DESCRIPTION OF PREFERRED EMBODIMENTS

Fast absorbing biocompatible copolymers having a proportion of units derived from tricarboxylic acids and a proportion of units derived from triols are prepared in accordance with the methods described herein. The copolymers are advantageous for use in surgical articles because the degradation products of the copolymers are nontoxic. The copolymers can be used as components in the manufacture of various surgical articles to be placed at or near a wound site in a body such as, coatings on sutures, wound healing gels, wound dressings and a variety of biomedical implants. The copolymers having units derived from tricarboxylic acids and triols can be synthesized by customary methods known by those with skill in the art. For example, the copolymers may be obtained by melt phase polymerization of a tricarboxylic acid and a triol in the presence of an organic esterification catalyst such as p-toluenesulphonic add. See, for example, "Synthesis and Biodegradation of Copolyesters from Citric Acid and Glycerol", *Polymer Bulletin*, Vol. 19, pp. 365–370 (1980).

Preferred tricarboxylic acids are Kreb's cycle tricarboxylic adds which include citric acid, cis-aconitic acid and isocitric acid. The most preferred tricarboxylic acid is citric acid. Preferred triols for preparing the copolymers described herein are glycerol, triethanolamine and diethylethanolamine (DEAE)-propanediol.

The units derived from a tricarboxylic acid are present in an amount from about 1 to about 99 weight percent based on the weight of the final copolymer. Preferably, the tricarboxylic acid units are present in an amount between about 30 and about 70 weight percent of the copolymer.

The units derived from a triol are present in an amount from about 1 to about 99 weight percent based on the weight of the final copolymer. Preferably, the triol units are present in an amount between about 30 and about 70 weight percent of the copolymer. In a particularly useful embodiment, the tricarboxylic acid is citric acid and the units derived therefrom are present in an amount from about 30 to about 70 weight percent and the triol is glycerol and the units derived therefrom are present in an amount from about 30 to about 70 weight percent. In another embodiment, monomeric units derived from citric acid are present in an amount from about 30 to about 70 weight percent and monomeric units derived from DEAE-propanediol are present in an amount from about 30 to about 70 weight percent. In still another embodiment, units derived from citric acid constitute from about 30 to about 50 weight percent and units derived from triethanolamine constitute from about 50 to about 70 weight percent.

The tricarboxylic acid and triol monomers are trifunctional. Specifically, the tricarboxylic acid monomers have three reactive carboxyl groups and the triol monomers have three reactive hydroxyl groups. Therefore, polymerization of these trifunctional monomers under heat and vacuum results in cross-linked copolymers.

If desired, water can be added to the cross-linked copolymer to produce a hydrogel. The amount of water employed will normally range from about 1 mole to about 20 moles per mole of polymer. While water is preferred to effect formation of the cross-linked gel it should be understood that other compounds can also be employed either together with or instead of water. Such compounds include polar organic solvents, such as ethanol, acetone, methanol, DMSO, etc. When the composition is intended for implantation it is possible to effectuate formation of a cross-linked gel in situ using the water naturally present in a mammalian body or with added water. However, to more precisely control the conditions and extent of cross-linking it is preferred to form the cross-linked gel prior to its use as an implant.

In another aspect, the copolymers derived from tricarboxylic acid and triol monomers have a surface charge for promoting tissue growth. A tricarboxylic acid can be reacted with a trialcoholamine to yield a copolymer having an inherent positive surface charge. For example, a copolymer having a net positive surface charge can be formed by copolymerizing citric acid and triethanolamine. Alternatively, a charge inducing functional group or substituent can be added to a triol prior to polymerization with the tricarboxylic acid. Normally from about 0.2 to about 0.8 moles of charge inducing reactant are employed per mole of the alcohol component to form a substituted triol. The alcohol is normally dissolved in a solvent and added dropwise to a solution of the charge inducing reactant. Stirring and heating temperatures of about 100° C. can facilitate the reaction. The substituent laden triol is then copolymerized with tricarboxylic acid to generate a copolymer having a net charge on its surface. Preferred functional groups are those having a positive charge at physiological pH. Amines can be used to impart a positive charge to the surface of the copolymer. A preferred positively charged functional group is diethylethanolamine (DEAE). For example, DEAE can be covalently attached to propanediol by methods known to those skilled in the art to produce DEAE-propanediol. DEAE-propanediol is then polymerized with a tricarboxylic acid, such as citric acid, to produce a citric acid/DEAE-propanediol copolymer. A citric acid/DEAE-propanediol derived copolymer is the most preferred copolymer having a net positive surface charge produced in accordance with the methods described herein.

The positively charged reactant promotes soft tissue growth in vivo. Thus, the copolymers derived from tricarboxylic acid and triol monomers having a net positive surface charge provide desirable compounds for use as surgical articles for promoting wound healing and repair of tissue defects. It is also known that negatively charged functional groups promote the growth of hard tissue such as bone. For example, a carboxymethyl group may be employed to impart a negative surface charge to the copolymers described herein. The mechanisms which cause charged functional groups to promote tissue growth have not yet been fully elucidated. The charged functional group may alter cell surface moieties of undifferentiated cells to promote expression of fibroblastic or osteogenic potential. In addition, specific substances or growth factors may bind to the charged polymeric material to effect the formation of new tissue.

Following the formation of a copolymer having a net surface charge, the copolymer can be hydrated to obtain a cross-linked gel. These cross-linked gels are useful surgical articles which are administered in vivo to promote wound healing and correct tissue defects.

The bioabsorbable copolymers having units derived from tricarboxylic acids and triols described herein can be used in the fabrication in whole or in part of a variety of surgical articles. These include but are not limited to suture coatings, staples, clips and other fasteners, wound dressings, drug delivery devices, pins, screws, gels, particularly wound healing gels, and other implants.

The copolymers obtained in accordance with the methods described herein may be formed into surgical articles using any known technique, such as, for example, extrusion, molding and/or solvent casting. The copolymers may be used alone, blended with other absorbable compositions, or in combination with non-absorbable components.

It is further within the scope of this invention to incorporate one or more medico-surgically useful substances, e.g., those which accelerate or beneficially modify the healing process when particles are applied to a surgical repair site, into surgical devices made in accordance with the present invention. The surgical device can carry a therapeutic agent which will be deposited at the repair site. For example, when a cross-linked gel having therapeutic agents within its meshwork is administered to an organism, such as a mammal, the meshwork expands releasing the therapeutic agent. The therapeutic agent can be chosen for its antimicrobial properties, capability for promoting repair or reconstruction and/or new tissue growth. Antimicrobial agents such as broad spectrum antibiotic (gentamicin sulfate, erythromycin or VX glycopeptides) which are slowly released into the tissue can be applied in this manner to aid in combating clinical and sub-clinical infections in a tissue repair site. To promote repair and/or tissue growth, one or several growth promoting factors can be introduced into the gels or other surgical articles, e.g., fibroblast growth factor bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasmainogen activator to cause thrombosis, superoxide dimutase to scavenge tissue damaging free radicals, tumor necrosis factor for cancer therapy or colony stimulating factor and interferon, interleukin-2 or other lymphokine to enhance the immune system. It is also contemplated that the medico-surgically useful substance may enhance blood coagulation. Thrombin is one such substance.

The bioabsorbable copolymers of the invention can be applied to a suture by any suitable process, e.g., passing the suture through a solution of the copolymer, e.g., in acetone, methylene chloride, etc., past a brush or other coating solution applicator, or past one or more spray nozzles dispensing the suture coating solution. The suture wetted with the coating solution is subsequently passed through or held in a drying oven for a time and at a temperature sufficient to vaporize and drive off the solvent. If desired, the suture coating composition can optionally contain additional components, e.g., dyes, antibiotics, antiseptics, growth factors, anti-inflammatory agents, etc.

Surgical articles made in part from the polymers described herein can be used to secure tissue in a desired position. Suture 101, may be attached to a surgical needle 100 as shown in FIG. 1 by methods well known in the art. Wounds may be sutured by approximating tissue and passing the needled suture through tissue to create wound closure. The needle is then preferably removed from the suture and the suture tied.

The following examples are illustrative of the copolymers of the present invention and surgical articles made therefrom.

EXAMPLE 1

Reaction of Citric Acid and Glycerol

A copolymer of citric acid and glycerol was obtained as follows:

A mixture of 33.8 grams of citric acid, 18.4 grams of glycerol, 0.42 grams of p-toluenesulphonic acid, and 100 ml of benzene was refluxed and heated with a Dean-Stark extractor to collect aziotropic $H_2O$ and benzene. The polymer was then placed under vacuum at 90° C. for 24 hours. The polymer was cooled and 1 liter of $H_2O$ was added to the polymer resulting in the formation of a cross-linked gel.

EXAMPLE 2

Degradation of Copolymer

Ten samples containing 0.1 grams of the citric acid/glycerol copolymer gel of Example 1 were prepared. 10 ml of saline was added per day to each sample. After 7–8 days at 37° C. each sample was dissolved.

EXAMPLE 3

Reaction of Citric Acid and DEAE-propanediol

A copolymer of citric acid and DEAE-propanediol was obtained as follows:

A mixture of 33.8 grams citric acid, 29.4 grams DEAE-propanediol, 0.42 grams of p-toluenesulphonic acid, and 100 ml of benzene was refluxed and heated with a Dean-Stark extractor to collect aziotropic $H_2O$ and benzene. The polymer was then placed under vacuum at 90° C. for 24 hours. The polymer was cooled and 1 liter of $H_2O$ was added to the polymer resulting in the formation of a cross-linked gel.

EXAMPLE 4

Reaction of Citric Acid and Triethanolamine

A cross-linked gel of citric acid and triethanolamine was obtained as follows:

55.7 grams (0.3 moles) of citric acid, 57.64 grams (0.3 moles) of triethanolamine and 285 mg (1.5 mmoles) of p-toluenesulphonic acid were added to a reactor equipped with a mechanical stirrer. The reactor was placed under vacuum and heated to 145°–150° C. resulting in the formation of a melt. After 15 minutes at 155° C., the melt became clear and colorless. Following an additional 25 minutes, the temperature was decreased to 100° C. and the mixture was stirred under vacuum for 17 hours. The resulting polymer was poured into a crystallizing dish and heated to 110° C. under vacuum for 3 hours. The dish was removed from the oven and cooled followed by the addition of 1 liter of $H_2O$ resulting in the formation of a gel. The gelled mixture was placed in a 2 liter flask, filtered, suspended with 1 liter of $H_2O$, and filtered two additional times. The gelled mass was then suspended in 1 liter of acetone. A subsequent acetone wash resulted in a light yellow solid copolymer which was placed under vacuum at 40° C. overnight to yield 43.7 grams (45% yield) of a granular light yellow solid.

It will be understood that various modifications may be made to the embodiments disclosed herein. One with skill in the art can employ other methods for obtaining copolymers having units derived from tricarboxylic acids and triols as well as related copolymers. As another example, copolymers having units derived from tricarboxylic acids and triols can be blended or combined with other bioabsorbable or nonabsorbable materials. Other copolymers derived from carboxylic acids and alcohols can also be prepared using the methods disclosed herein. Therefore, the above description should not be construed as limiting, but merely as exemplifications of preferred embodiments. Those skilled in the art will envision other modifications within the scope and spirit of the claims appended hereto.

What is claimed is:

1. A bioabsorbable copolymer comprising:
   a) monomeric units derived from a tricarboxylic acid; and
   b) monomeric units derived from a triol wherein at least a portion of the units derived from a triol includes a substituent selected from the group consisting of amine and carboxymethyl groups.

2. A bioabsorbable copolymer according to claim 1 wherein the substituent is an amine group which imparts a net positive surface charge upon the copolymer.

3. A copolymer according to claim 1 wherein the tricarboxylic acid derived units are present in an amount of about 30 to 70 weight percent.

4. A copolymer according to claim 1 wherein the triol derived units are present in an amount of about 30 to 70 weight percent.

5. A copolymer according to claim 1 wherein the tricarboxylic acid is selected from the group consisting of citric acid, cis-aconitic acid and isocitric acid.

6. A bioabsorbable copolymer comprising:
   a) monomeric units derived from a tricarboxylic acid; and
   b) monomeric units derived from a triol selected from the group consisting of triethanolamine and DEAE-propanediol.

7. A copolymer according to claim 6 wherein the monomeric units derived from a tricarboxylic acid comprise about 30 to about 70 weight percent of the copolymer and the monomeric units derived from a triol comprise about 30 to about 70 weight percent of the copolymer.

8. A copolymer according to claim 7 wherein the tricarboxylic acid is citric acid.

9. A copolymer according to claim 7 wherein the triol is triethanolamine.

10. A copolymer according to claim 8 wherein the triol is triethanolamine.

11. A copolymer according to claim 7 wherein the triol is DEAE-propanediol.

12. A copolymer according to claim 8 wherein the triol is DEAE-propanediol.

13. A composition comprising the bioabsorbable copolymers of claim 1 and a therapeutic agent selected from the group consisting of antimicrobial agents, growth promoting factors, kidney plasminogen activator, superoxide dimutase, tumor necrosis factor, colony stimulating factor, lymphokines and thrombin.

14. A hydrogel comprising the bioabsorbable copolymer of claim 1.

15. A composition comprising the bioabsorbable copolymer of claim 6 and a therapeutic agent selected from the group consisting of anti microbial agents, growth promoting factors, kidney plasminogen activator, superoxide dimutase, tumor neurosis factor, colony stimulating factor, lymphokines and thrombin.

16. A hydrogel comprising the bioabsorable copolymer of claim 6.

* * * * *